United States Patent
Bagley et al.

(10) Patent No.: US 12,213,663 B2
(45) Date of Patent: Feb. 4, 2025

(54) SUTURE NEEDLE DEVICES AND SUTURE ATTACHMENT METHODS

(71) Applicant: Boston Scientific Scimed, Inc., Maple Grove, MN (US)

(72) Inventors: Kevin Bagley, Natick, MA (US); Shaun Comee, Fiskdale, MA (US); Christopher Deuel, Melrose, MA (US); Stanley Gilbert, Litchfield, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/156,650

(22) Filed: Jan. 19, 2023

(65) Prior Publication Data
US 2023/0149013 A1    May 18, 2023

Related U.S. Application Data

(63) Continuation of application No. 16/561,232, filed on Sep. 5, 2019, now abandoned.
(Continued)

(51) Int. Cl.
*A61B 17/04* (2006.01)
*A61B 17/00* (2006.01)
*A61B 17/06* (2006.01)

(52) U.S. Cl.
CPC ...... *A61B 17/0469* (2013.01); *A61B 17/0482* (2013.01); *A61B 17/06066* (2013.01);
(Continued)

(58) Field of Classification Search
CPC .......... A61B 17/06066; A61B 17/0469; A61B 17/0482; A61B 17/06004; A61B 17/0401;
(Continued)

(56) References Cited

U.S. PATENT DOCUMENTS 3,880,167 A * 4/1975 Hardwick ........ A61B 17/06004
606/225
5,358,498 A    10/1994 Shave
(Continued)

FOREIGN PATENT DOCUMENTS

CA        2682488 A1    10/2008
DE    202005022017 U1    5/2012
(Continued)

OTHER PUBLICATIONS

International Search Report and Written Opinion of the International Search Authority dated Mar. 9, 2021, issued in corresponding International Application No. PCT/US2019/049683, filed Sep. 5, 2019 (11 pages).
(Continued)

*Primary Examiner* — Katherine H Schwiker
*Assistant Examiner* — Lauren Dubose
(74) *Attorney, Agent, or Firm* — Seager, Tufte & Wickhem, LLP

(57) ABSTRACT

According to one aspect, a medical device including a needle configured for use in suturing tissue is described. The needle may include a cylindrical body having a longitudinal axis extending between first and second ends of the cylindrical body. The needle may also include a lumen extending through the cylindrical body transverse to the longitudinal axis. The needle may further include a first end portion at the first end of the cylindrical body. The first end portion may include a sharp point configured to pierce tissue. An outer surface of the cylindrical body may define a first recess in communication with an opening of the lumen and configured to receive an end of a suture.

20 Claims, 3 Drawing Sheets

Related U.S. Application Data

(60) Provisional application No. 62/848,885, filed on May 16, 2019, provisional application No. 62/727,783, filed on Sep. 6, 2018.

(52) U.S. Cl.
CPC ............... *A61B 2017/00477* (2013.01); *A61B 2017/0474* (2013.01); *A61B 2017/06038* (2013.01); *A61B 2017/06047* (2013.01); *A61B 2017/0609* (2013.01); *A61B 2017/061* (2013.01)

(58) Field of Classification Search
CPC .. A61B 2017/0609; A61B 2017/06047; A61B 2017/061; A61B 2017/06019; A61B 2017/00477; A61B 2017/045; A61B 2017/0053; A61B 1/00101; A61B 2017/06009

See application file for complete search history.

(56) References Cited

U.S. PATENT DOCUMENTS

| | | |
|---|---|---|
| 5,478,344 A | 12/1995 | Stone et al. |
| 5,584,861 A | 12/1996 | Swain et al. |
| 5,674,229 A | 10/1997 | Tovey et al. |
| 5,693,071 A | 12/1997 | Gorecki et al. |
| 5,865,836 A | 2/1999 | Miller |
| 6,086,608 A | 7/2000 | Ek et al. |
| 6,152,935 A | 11/2000 | Kammerer et al. |
| 6,200,329 B1 | 3/2001 | Fung et al. |
| 6,494,888 B1 | 12/2002 | Laufer et al. |
| 6,506,196 B1 | 1/2003 | Laufer |
| 6,554,845 B1 | 4/2003 | Fleenor et al. |
| 6,569,085 B2 | 5/2003 | Kortenbach et al. |
| 6,626,917 B1 | 9/2003 | Craig |
| 6,663,639 B1 | 12/2003 | Laufer et al. |
| 6,719,763 B2 | 4/2004 | Chung et al. |
| 6,740,030 B2 | 5/2004 | Martone et al. |
| 6,746,457 B2 | 6/2004 | Dana et al. |
| 6,755,843 B2 | 6/2004 | Chung et al. |
| 6,773,441 B1 | 8/2004 | Laufer et al. |
| 6,808,491 B2 | 10/2004 | Kortenbach et al. |
| 6,821,285 B2 | 11/2004 | Laufer et al. |
| 6,835,200 B2 | 12/2004 | Laufer et al. |
| 6,908,427 B2 | 6/2005 | Fleener et al. |
| 6,997,931 B2 | 2/2006 | Sauer et al. |
| 7,056,284 B2 | 6/2006 | Martone et al. |
| 7,063,710 B2 | 6/2006 | Takamoto et al. |
| 7,063,715 B2 | 6/2006 | Onuki et al. |
| 7,094,246 B2 | 8/2006 | Anderson et al. |
| 7,144,401 B2 | 12/2006 | Yamamoto et al. |
| 7,147,646 B2 | 12/2006 | Dana et al. |
| 7,153,314 B2 | 12/2006 | Laufer et al. |
| 7,220,266 B2 | 5/2007 | Gambale |
| 7,232,445 B2 | 6/2007 | Kortenbach et al. |
| 7,235,086 B2 | 6/2007 | Sauer et al. |
| 7,326,221 B2 | 2/2008 | Sakamoto et al. |
| 7,344,545 B2 | 3/2008 | Takemoto et al. |
| 7,347,863 B2 | 3/2008 | Rothe et al. |
| 7,361,180 B2 | 4/2008 | Saadat et al. |
| 7,517,357 B2 | 4/2009 | Abrams et al. |
| 7,530,985 B2 | 5/2009 | Takemoto et al. |
| 7,601,161 B1 | 10/2009 | Nobles et al. |
| 7,618,425 B2 | 11/2009 | Yamamoto et al. |
| 7,713,277 B2 | 5/2010 | Laufer et al. |
| 7,722,633 B2 | 5/2010 | Laufer et al. |
| 7,727,246 B2 | 6/2010 | Sixto, Jr. et al. |
| 7,736,373 B2 | 6/2010 | Laufer et al. |
| 7,776,057 B2 | 8/2010 | Laufer et al. |
| 7,776,066 B2 | 8/2010 | Onuki et al. |
| 7,842,051 B2 | 11/2010 | Dana et al. |
| 7,846,180 B2 | 12/2010 | Cerier |
| 7,857,823 B2 | 12/2010 | Laufer et al. |
| 7,896,893 B2 | 3/2011 | Laufer et al. |
| 7,918,867 B2 | 4/2011 | Dana et al. |
| 7,951,157 B2 | 5/2011 | Gambale |
| 7,992,571 B2 | 8/2011 | Gross et al. |
| 7,993,368 B2 | 8/2011 | Gambale et al. |
| 8,016,840 B2 | 9/2011 | Takemoto et al. |
| 8,021,376 B2 | 9/2011 | Takemoto et al. |
| 8,057,494 B2 | 11/2011 | Laufer et al. |
| 8,062,314 B2 | 11/2011 | Sixto, Jr. et al. |
| 8,066,721 B2 | 11/2011 | Kortenbach et al. |
| 8,105,355 B2 | 1/2012 | Page et al. |
| 8,211,123 B2 | 7/2012 | Gross et al. |
| 8,216,253 B2 | 7/2012 | Saadat et al. |
| 8,226,667 B2 | 7/2012 | Viola et al. |
| 8,277,468 B2 | 10/2012 | Laufer et al. |
| 8,287,554 B2 | 10/2012 | Cerier et al. |
| 8,287,556 B2 | 10/2012 | Gilkey et al. |
| 8,308,765 B2 | 11/2012 | Saadat et al. |
| 8,313,496 B2 | 11/2012 | Sauer et al. |
| 8,361,089 B2 | 1/2013 | Chu |
| 8,388,632 B2 | 3/2013 | Gambale et al. |
| 8,425,555 B2 | 4/2013 | Page et al. |
| 8,454,631 B2 | 6/2013 | Viola et al. |
| 8,480,691 B2 | 7/2013 | Dana et al. |
| 8,540,735 B2 | 9/2013 | Mitelberg et al. |
| 8,551,120 B2 | 10/2013 | Gambale |
| 8,585,720 B2 | 11/2013 | Gross et al. |
| 8,632,553 B2 | 1/2014 | Sakamoto et al. |
| 8,679,136 B2 | 3/2014 | Mitelberg |
| 8,709,022 B2 | 4/2014 | Stone et al. |
| 8,764,771 B2 | 7/2014 | Chu |
| 8,882,785 B2 | 11/2014 | DiCesare et al. |
| 8,926,634 B2 | 1/2015 | Rothe et al. |
| 8,992,570 B2 | 3/2015 | Gambale et al. |
| 9,011,466 B2 | 4/2015 | Adams et al. |
| 9,089,325 B2 | 7/2015 | Mitelberg et al. |
| 9,125,646 B2 | 9/2015 | Woodard, Jr. et al. |
| 9,198,562 B2 | 12/2015 | Mitelberg et al. |
| 9,320,515 B2 | 4/2016 | Dana et al. |
| 9,486,126 B2 | 11/2016 | West et al. |
| 9,504,465 B2 | 11/2016 | Chu |
| 9,510,817 B2 | 12/2016 | Saadat et al. |
| 9,549,728 B2 | 1/2017 | Chu |
| 9,750,494 B2 | 9/2017 | Gross et al. |
| 9,788,831 B2 | 10/2017 | Mitelberg et al. |
| 9,844,366 B2 | 12/2017 | Woodard, Jr. et al. |
| 9,867,610 B2 | 1/2018 | Mitelberg et al. |
| 10,045,871 B2 | 8/2018 | Saadat et al. |
| 10,143,463 B2 | 12/2018 | Dana et al. |
| 10,194,902 B2 | 2/2019 | Nobles et al. |
| 10,335,142 B2 | 7/2019 | Raybin et al. |
| 2002/0107530 A1 | 8/2002 | Sauer et al. |
| 2003/0204205 A1 | 10/2003 | Sauer et al. |
| 2004/0002699 A1 | 1/2004 | Ryan et al. |
| 2004/0138706 A1 | 7/2004 | Abrams et al. |
| 2005/0033319 A1 | 2/2005 | Gambale et al. |
| 2005/0250985 A1 | 11/2005 | Saadat et al. |
| 2006/0069399 A1 | 3/2006 | Weisel et al. |
| 2006/0282094 A1 | 12/2006 | Stokes et al. |
| 2007/0219586 A1 | 9/2007 | Mahadevan |
| 2007/0270908 A1 | 11/2007 | Stokes et al. |
| 2008/0086148 A1 | 4/2008 | Baker et al. |
| 2008/0108957 A1 | 5/2008 | Cumbo |
| 2009/0043335 A1 | 2/2009 | Capurro |
| 2009/0177031 A1 | 7/2009 | Surti et al. |
| 2010/0030239 A1 | 2/2010 | Viola et al. |
| 2010/0137681 A1 | 6/2010 | Ewers et al. |
| 2010/0174299 A1 | 7/2010 | Viola et al. |
| 2010/0198006 A1 | 8/2010 | Greenburg et al. |
| 2011/0060352 A1 | 3/2011 | Chu |
| 2012/0083838 A1 | 4/2012 | Okoniewski et al. |
| 2012/0150200 A1* | 6/2012 | Mitelberg ............... A61B 1/04 606/147 |
| 2012/0158023 A1 | 6/2012 | Mitelberg et al. |
| 2012/0271327 A1 | 10/2012 | West et al. |
| 2013/0096581 A1 | 4/2013 | Gilkey et al. |
| 2013/0096583 A1 | 4/2013 | Mueller et al. |
| 2013/0304093 A1 | 11/2013 | Serina et al. |
| 2014/0121457 A1 | 5/2014 | Mori et al. |

(56) References Cited

U.S. PATENT DOCUMENTS

| | | |
|---|---|---|
| 2014/0128668 A1 | 5/2014 | Cox et al. |
| 2015/0126983 A1 | 5/2015 | Alvarado et al. |
| 2016/0045197 A1 | 2/2016 | Mitelberg et al. |
| 2017/0042534 A1 | 2/2017 | Nobles et al. |
| 2017/0086817 A1 | 3/2017 | Mitelberg |
| 2017/0086818 A1 | 3/2017 | Mitelberg |
| 2017/0119371 A1 | 5/2017 | Mims et al. |
| 2017/0319197 A1 | 11/2017 | Gross et al. |
| 2018/0042602 A1 | 2/2018 | Mitelberg et al. |
| 2018/0042603 A1 | 2/2018 | Mitelberg et al. |
| 2018/0153381 A1 | 6/2018 | Wei et al. |
| 2018/0221009 A1 | 8/2018 | Mitelberg et al. |
| 2018/0235604 A1 | 8/2018 | Comee et al. |
| 2018/0317904 A1* | 11/2018 | Malkowski ........ A61B 17/0469 |
| 2018/0344501 A1 | 12/2018 | Saadat et al. |

FOREIGN PATENT DOCUMENTS

| | | | |
|---|---|---|---|
| EP | 1520509 A1 | 4/2005 | |
| EP | 2108304 A2 | 10/2009 | |
| JP | S5216294 U | 2/1977 | |
| JP | H04227243 A | 8/1992 | |
| JP | H07155332 A | 4/2005 | |
| JP | 2006515203 A | 5/2006 | |
| JP | 2009226224 A | 1/2012 | |
| JP | 2014514017 A | 6/2014 | |
| JP | 7130852 B2 | 9/2022 | |
| WO | 0189393 A1 | 11/2001 | |
| WO | 2008016592 A2 | 2/2008 | |
| WO | 2008045376 A2 | 4/2008 | |
| WO | 2008098124 A1 | 8/2008 | |
| WO | 2010036227 A1 | 4/2010 | |
| WO | WO-2014165221 A1 * | 10/2014 | ....... A61B 17/06004 |
| WO | 2016200811 A1 | 12/2016 | |
| WO | 2017087856 A1 | 5/2017 | |
| WO | 2018156603 A1 | 8/2018 | |

OTHER PUBLICATIONS

Office Action in Japan Application No. 2021-510964, dated Jun. 2, 2023 (8 pages).

International Search Report and Written Opinion dated Aug. 20, 2019 for International Application No. PCT/US2019/033748.

International Search Report and Written Opinion dated Dec. 6, 2019 for International Application No. PCT/US2019/037995.

International Search Report and Written Opinion dated Nov. 18, 2019 for International Application No. PCT/US2019/049774.

International Search Report and Written Opinion dated Oct. 1, 2019 for International Application No. PCT/US2019/038006.

International Search Report and Written Opinion dated Sep. 20, 2019 for International Application No. PCT/US2019/039312.

Invitation to Pay Additional Fees dated Sep. 26, 2019 for International Application No. PCT/US2019/037995.

* cited by examiner

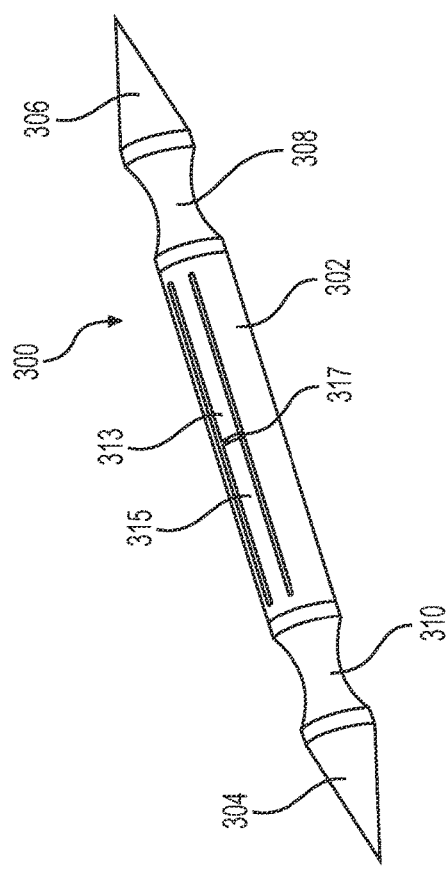
FIG. 3
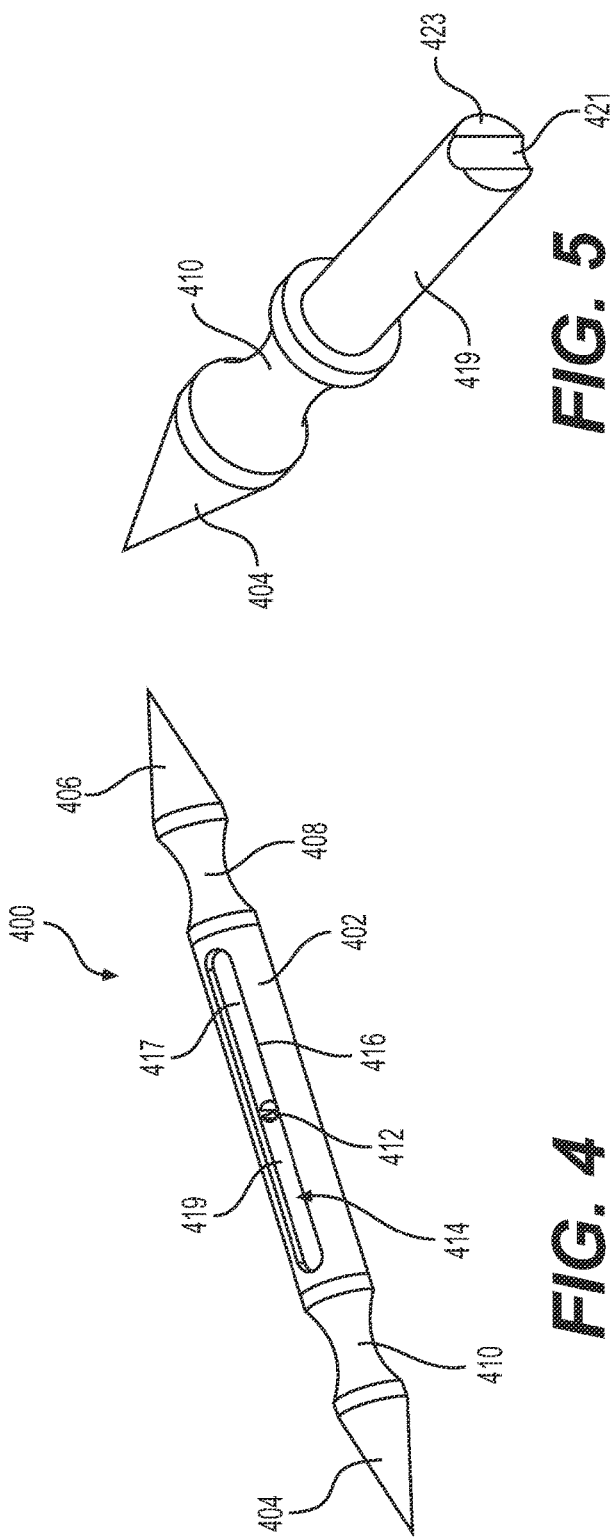
FIG. 5
FIG. 4

SUTURE NEEDLE DEVICES AND SUTURE ATTACHMENT METHODS

CROSS-REFERENCE TO RELATED APPLICATIONS

This application is a continuation of U.S. application Ser. No. 16/561,232, filed on Sep. 5, 2019, and now pending, which claims the benefit of priority from U.S. Provisional Application No. 62/727,783, filed on Sep. 6, 2018, and U.S. Provisional Application No. 62/848,885, filed on May 16, 2019, each of which is incorporated by reference herein in its entirety.

TECHNICAL FIELD

The present disclosure relates generally to medical devices and related methods. More particularly, the present disclosure relates to needles for use in suturing tissue, related assemblies including a suture, methods for attaching a suture to a needle, and methods for joining tissue, among other aspects.

BACKGROUND

In some medical procedures, it may be necessary or useful to fixedly connect a portion of tissue to another portion of tissue. Attaching portions of tissue, such as to hold together a wound or damaged tissue, with one or more sutures may allow adhesions to form between the two tissues so that the attachment remains after the sutures are absorbed or removed. Often, an assembly including a needle and a suture coupled to the needle is used to suture tissue together. The tissue attachment method often involves piercing tissue with the needle and pulling on the needle to pull or thread a suture attached to the needle through the hole created in the tissue. One way to couple a suture to a needle involves a hole in the needle in which the suture is thread through, and a knot may be tied at one end of the suture to prevent the end from passing through the hole of the needle. However, knot size can be inconsistent and may, in some examples, pull through the hole in the needle and uncouple the needle and suture. When a suture uncouples from a needle, surgical operation times may increase, as operators may need to reassemble the needle and suture assembly. This and other suture attachment means may allow the suture to extend radially outward from the needle, increasing resistance as the needle is pushed through tissue. Thus, there is a need for alternative suture and needle assemblies and methods of suturing tissue to, for example, decrease the chance of the suture releasing from the needle, ease the passing of the needle and suture through tissue, and/or simplify suturing procedures.

SUMMARY

Embodiments of the present disclosure relate to, among other things, medical devices for suturing tissue. The present disclosure also relates to methods of attaching a suture to medical devices (including needles), methods of operating the devices, and/or performing procedures with the devices. Each of the embodiments disclosed herein may include one or more of the features described in connection with any of the other disclosed embodiments.

According to one aspect, a medical device including a needle configured for use in suturing tissue. The needle may include a cylindrical body having a longitudinal axis extending between first and second ends of the cylindrical body. The needle may also include a lumen extending through the cylindrical body transverse to the longitudinal axis. The needle may further include a first end portion at the first end of the cylindrical body. The first end portion may include a sharp point configured to pierce tissue. An outer surface of the cylindrical body may define a first recess in communication with an opening of the lumen and configured to receive an end of a suture.

The medical device may include one or more of the features below. The needle may include a second end portion at the second end of the cylindrical body, and the second end portion may include a sharp point configured to pierce tissue. The first recess may form a slot in the exterior surface of the cylindrical body, and the first recess may be configured to receive a formed end portion of a suture. The needle may further include a second recess in communication with a second opening of the lumen, and the second recess may be configured to receive a portion of the suture adjacent the end of the suture. The first recess may be a counterbore surrounding the opening of the lumen According to other aspects of the present disclosure, a medical device, may include a needle configured for use in suturing tissue. The needle may include a cylindrical body having first and second ends. The needle may also include an opening defined by the cylindrical body and may be configured to receive a suture. The needle may further include a first end portion at one of the first or second ends of the cylindrical body. The first end portion may include a sharp point configured to pierce tissue. The cylindrical body may include a first tab extending from the first end of the cylindrical body to the opening and may be configured to bend to secure a suture within the body.

The medical device may also include one or more of the features below. The cylindrical body may include a second tab extending from the second end of the cylindrical body to the opening. The opening may include at least a portion transverse to a longitudinal axis of the cylindrical body. The opening may be H-shaped, each tab may extend longitudinally on the cylindrical body, and each tab may be configured to bend at a portion of the tab proximate an end of cylindrical body.

According to other aspects of the present disclosure, a medical device may include a needle configured for use in suturing tissue. The needle may include a cylindrical body including a first lumen extending longitudinally within the body to a first end of the body. The needle may also include a first end portion extending from the first end of the cylindrical body. The first end portion may include a first sharp point configured to pierce tissue, and a first extension may extend within the first lumen of the cylindrical body. The first end portion may be configured to engage a suture to secure the suture within the first lumen of cylindrical body.

The medical device may also include one or more of the features below. The needle may further include a second end portion extending from a second end of the cylindrical body opposing the first end. The second end portion may include a second sharp point configured to pierce tissue and a second extension may extend within the first lumen of the cylindrical body. The first extension may be cylindrical, may be configured to be positioned within the first lumen of the cylindrical body, and may include a first end face at an end opposite the sharp point of the first end. The second extension may be cylindrical, may be configured to be positioned within the first lumen of the cylindrical body, and may include a second end face at an end opposite the sharp point of the second end. The first and second extensions may be configured to couple a suture to the cylindrical body by positioning a suture between the first and second end faces. The first end face and the second end face may be contoured to form an opening between the first and second end faces when the first and second extensions are positioned in the first lumen. The opening may be configured to receive an end portion of a suture with a diameter larger than the opening. The cylindrical body and the first end portion may be integrally formed. The first end portion may include a first concave portion between the first sharp point and the first extension. The second end portion may include a second concave portion between the second sharp point and the second extension. The first extension of the first end portion may include a first portion, a second portion, and a second lumen between the first and second portions. The second lumen may be configured to receive a suture. The first extension may have a cross-sectional diameter larger than the cross-sectional diameter of the lumen of the cylindrical body. The diameter of the second lumen of the first extension may be configured to be smaller than the diameter of a suture positioned within the second lumen. The first extension may be a collet. The diameter of the second lumen of the first extension may be configured to decrease when the first extension is positioned within cylindrical body.

The foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows:

FIG. 3 illustrates a perspective view of an exemplary medical device, according to aspects of this disclosure.

FIG. 4 illustrates a perspective view of an exemplary medical device, according to aspects of this disclosure.

FIG. 5 illustrates a perspective view of a portion of the medical device of FIG. 4, according to aspects of this disclosure.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. When used herein, the terms "approximately" and "substantially" may indicate a range of values within +/−5% of a stated value.

Figure 1A:
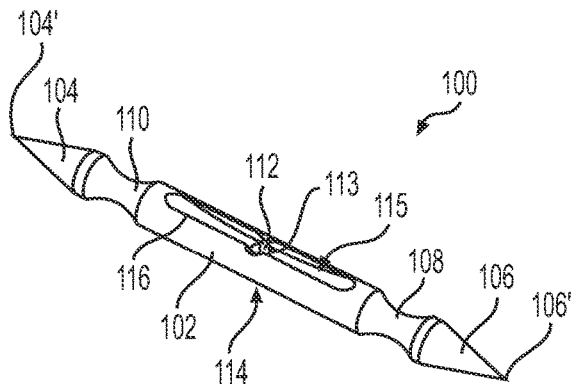
FIG. 1A illustrates a perspective view of an exemplary medical device, according to aspects of this disclosure.

FIG. 1A illustrates a perspective view of an exemplary medical device 100, shown as a double-sided needle. Medical device 100 may include a cylindrical body 102 and two end portions, or ends, 104, 106. Each end 104, 106, may be tapered and come to a sharp point 104', 106'. In other examples, medical device 100 may include a single sharp point (either 104' or 106' at one end 104, 106) and include a blunt opposing end (the other of 104, 106). In some examples, ends 104, 106 may include concave portions 108, 110. In other examples, ends 104, 106 may not include concave portions 108, 110 and may form a taper starting at an end of cylindrical body 102. Concave portions 108, 110, may have a curved outer surface that may curve radially inward relative to the longitudinal axis of medical device 100. In some examples, concave portions 108, 110, may have a curved exterior surface that may meet and be flush with cylindrical body 102 at an end of the curved surface. In some examples, concave portions 108, 110, may be hourglass shaped and may have an exterior surface that curves radially-inward relative to the exterior surface of cylindrical body 102. In some examples, concave portions 108, 110 may be equidistant from a lumen 112 of cylindrical body 102. In some examples, each concave portion 108, 110 may be configured to receive a bearing ball from a medical device. The portion of each end 104, 106, on the opposite end of sharp point 104', 106', may be coupled to the cylindrical body 102. In some examples, ends 104, 106 may be welded to cylindrical body 102.

Medical device 100 may also include a lumen 112 extending through cylindrical body 102. Lumen 112 may extend through a central portion of cylindrical body 102 (shown in FIG. 1) and may extend perpendicular to a longitudinal dimension of cylindrical body 102 that extends through sharp points 104', 106'. In other examples, lumen 112 may extend through a non-central portion of cylindrical body 102 and/or be at an angle transverse to the longitudinal dimension, but not perpendicular. Lumen 112 may include a first opening 113 on one side of cylindrical body 102 and a second opening 114 on the opposite side of cylindrical body 102 as the first opening 113. In some examples, cylindrical body 102 may include recesses or slots 115, 116 extending longitudinally on a radially-outer surface of cylindrical body 102. In some examples, slots 115, 116 may be positioned on opposite sides of cylindrical body 102. Slots 115, 116 may create recesses in cylindrical body 102. Opening 113 of lumen 112 may be positioned within or otherwise in communication with slot 115, and opening 114 may be positioned in or otherwise in communication with slot 116. Slots 115, 116 may taper radially inward from portions proximate to each longitudinal end of cylindrical body 102 to openings 113, 114. Slots 115, 116 may be configured to receive a melted end of a suture. In some examples, medical device 100 may be metal or any other suitable biocompatible material.

Figure 1B:
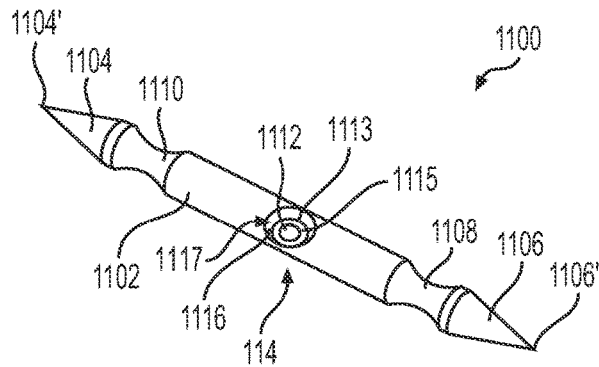
FIG. 1B illustrates a perspective view of an exemplary medical device, according to aspects of this disclosure.

FIG. 1B illustrates a perspective view of another exemplary medical device 1100, shown as a double-sided needle. Medical device 1100 may include cylindrical body 1102, two ends 1104, 1106 with sharp points 1104', 1106', concave portions 1108, 1110, lumen 1112, and opening 1113, similar to those shown in FIG. 1A, except for the following differences. Cylindrical body 1102 may include a single circular counter bore 1117 surrounding opening 1113 of lumen 1112. In other examples, single counter bore 1117 may surrounding opening 1114 (the opening at the other end of lumen 1112), or medical device 1100 may include two counter bores 1117 positioned at each opening 1113, 1114 of lumen 1112. In other examples, medical device 1100 may include a single counter bore 1117 at opening 1113, and opening 1114 may be flush with the exterior surface of cylindrical body 1102. Counter bore 1117 may include a wall 1116 extending radially inward from the radially-outermost surface of cylindrical body 1102 and a ridge 1115 positioned around opening 1113. Counter bore 1117 at one of openings 1113, 1114 may be configured to receive an end portion of a suture, such as a melted end portion of a suture that may conform to the shape of counterbore 1117. Counter bore 1117 may assist with preventing a suture from passing through lumen 1112.

Figure 1C:
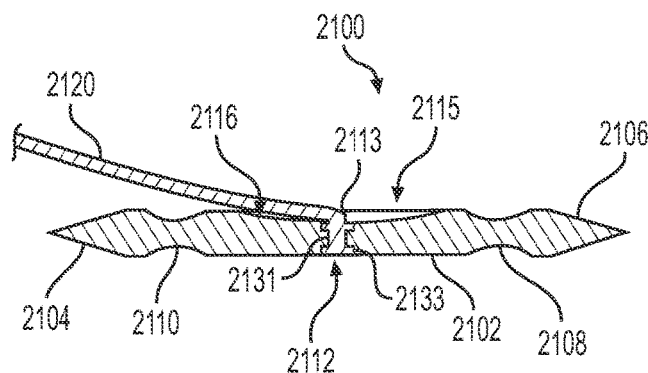
FIG. 1C is a cross sectional view of an exemplary medical device, according to aspects of the disclosure.

FIG. 1C illustrates a side cross-sectional view of another exemplary medical device 2100 similar to devices 100 and 1100. Medical device 2100 may include a cylindrical body 2102, two ends 2104, 2106, concave portions 2108, 2110, lumen 2112, opening 2113, and slots 2115, 2116. In some examples, a suture 2120 may be melted within lumen 2112. In some examples, suture 2120 may not extend beyond the opening of lumen 2112 on an opposite side of cylindrical body 2102 from slots 2115, 2116. In some examples, lumen 2112 may include one or more protrusions 2131 (each of which protrudes into lumen 2112) and/or one or more recesses 2133 adjacent the protrusions 2131. Each protrusion 2131 and/or recess 2133 may facilitate coupling suture 2120 to medical device 2100. For example, suture 2120 may be melted and/or deformed so that portions of suture 2110 may be positioned within one or more recesses 2133 of lumen 2112. After melting and/or deforming portions of suture 2120 to position portions of suture within one or more recesses 2133, the suture 2120 may be fixedly coupled to medical device 2100 such that suture remains within lumen 2112 when a pulling force is applied to the suture, such as when using medical device 2100 to suture a patient. Protrusions 2131 counter the pulling force on suture 2110 and assist in retaining suture 2110 in lumen 2112. Medical device 2100 may allow suture 2120 to be coupled to medical device 2100 and only extend from one opening 2113 of lumen 2112. As shown in FIG. 1C, suture 2120 may be bent at opening 2113 of lumen 2112 such that a portion of suture 2120 is positioned within a slot 2116, allowing for a smaller exterior diameter of medical device 2100. In other examples, lumen 2112 may include any number of protrusions and/or recesses and/or may include curved protrusions and/or recesses. In some examples, lumen 2112 may not extend completely through medical device 2100.

Figure 2A:
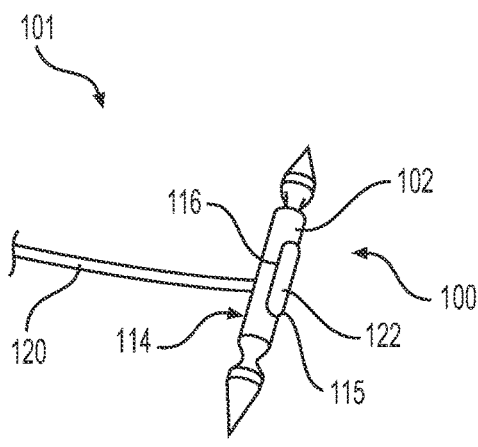
FIGS. 2A and 2B illustrate perspective views of an exemplary medical device assembly including the exemplary medical device of FIG. 1A, according to aspects of this disclosure.
Figure 2B:
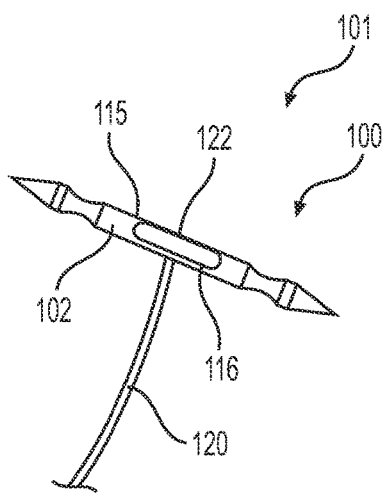

FIGS. 2A and 2B illustrate perspective views of an exemplary medical device assembly 101 including medical device 100 of FIG. 1A and a suture 120. Suture 120 may be cylindrical and may be polypropylene. In other examples, suture 120 may be polyester, nylon, polyglycolic acid, polylactic acid, polymer materials, or any other absorbable or non-absorbable biocompatible material. In medical device assembly 101, suture 120 may be positioned within lumen 112. The diameter of suture 120 may be sized to fit within lumen 112 and may have a diameter less than the diameter of lumen 112. An end portion 122 of suture 120 may be T-shaped and may be shaped to fit within either slot 115 or slot 116. The T-shape of end portion 122 may prevent suture 120 from being pulled out of lumen 112 during use. In some examples, the end portion 122 of suture 120 may be positioned within either of slots 115, 116, such that end portion 122 does not extend beyond the radially-outermost portion of the outer surface of cylindrical body 102. In some examples, the outer surface of end portion 122 may be flush with the outer surface of body 102. The slot 115, 116 that is not accommodating end portion 122 may be configured to receive suture 120 when suture 120 is bent to be approximately longitudinally aligned with/parallel with medical device 100, for example when a user is pushing medical device assembly 101 through tissue of a patient and suture 120 may be rotated at opening 113 of lumen and positioned within one of slots 115, 116 opposite the slot in which end portion 122 is positioned. Thus, slots 115, 116 may facilitate the insertion of medical device 100 into a patient by having little or no suture protruding radially outward of the outer surface of body 102.

In some examples, a method to assemble medical device assembly 101 includes heating an end portion of suture 120 such that the end portion melts and conforms to the shape of, and is contained within, one of slots 115, 116, for example to form end portion 122. When an end portion of suture 120 melts from heating, suture 120 may bond to medical device 100 (and particularly body 102) and may prevent suture 120 from moving away from medical device 100 during use. In some examples, end portion 122 of suture 120 may be conformed to the shape of one of slots 115, 116. In other examples, such as when coupling a suture to medical device 1100 of FIG. 1B, an end portion of a suture may be conformed to the shape of a circular shaped counter bore 1117 in medical device 1100 and extend through lumen 1112. In some examples, end portion 122 of suture 120 is fixedly attached to medical device 100. In operation, slots 115, 116 may facilitate medical device 100 movement through tissue by allowing suture 120 to be received within slots 115, 116 and prevent suture 120 from increasing the circumference, diameter, or cross-sectional diameter of cylindrical body 102 of medical device 100, which may prevent damage to tissue. Suture 120 may be used in medical device assemblies incorporating any of the medical devices described herein.

FIG. 3 illustrates a perspective view of an exemplary medical device 300 similar to medical device 100. Medical device 300 may include a cylindrical body 302 and end portions, or ends, 304, 306 coupled to ends of cylindrical body 302. Ends 304, 306 may include concave portions 308, 310. Cylindrical body 302 may be hollow and may include an opening 317. Opening 317 may be H-shaped and may provide access to the interior portion of cylindrical body 302. In some examples, opening 317 may include two slots 319, 321 extending longitudinally on cylindrical body 302 and one slot 323 connecting the two longitudinally-extending slots 319, 321 and transverse to each of the two longitudinally-extending slots 319, 321. In some examples, slot 323 may be positioned at the longitudinal midpoint of cylindrical body 302 and/or slots 319, 321. In some examples, slot 323 may be perpendicular to slots 319, 321. Cylindrical body 302 may include tabs or flanges 313, 315 that may be formed in the wall of cylindrical body 302. In some examples, tabs or flanges 313, 315 may extend longitudinally on cylindrical body 302, may extend from an end of body 302 to the transverse slit 323 of opening 317. In some examples, tabs or flanges 313, 315 may define opening 317 and/or be surrounded on at least three sides by opening 317. Flanges 315, 317 are cantilevered at, and can flex at, ends 315', 313' of flanges 315, 317 respectively. Flanges 315, 317 thereby can flex into and away from the hollow interior portion of body 302.

A suture (not shown) may be positioned within hollow cylindrical body 302 under tabs or flanges 313, 315. Tabs or flanges 313, 315 may be pressed down onto the suture by a user, crimping the suture in place by pushing the suture between one or more of tabs or flanges 313, 315 and an interior portion of hollow cylindrical body 302. In some examples, after a user pushes down one or more of tabs or flanges 313, 315, the one or more tabs or flanges 313, 315 yields and remains bent down and holding the suture in place. In some examples, tabs or flanges 313, 315 may provide a mechanical lock on a suture positioned within an interior portion of hollow cylindrical body 302 and/or may fixedly couple a suture to medical device 300, such as fixedly couple a suture within cylindrical body 302. In some examples, by allowing an end portion of a suture to be crimped within hollow cylindrical body 302, such as by bending one or more tabs or flanges 313, 315, will allow medical device 300 to be more streamlined and limit the outer diameter or cross-sectional dimension of cylindrical body 302 by providing a suture fastening mechanism entirely within cylindrical body 302, which may prevent excessive tissue damage when a user operates with medical device 300. Once a suture is coupled to medical device 300, suture may exit medical device 300 at opening 317.

Figure 7:
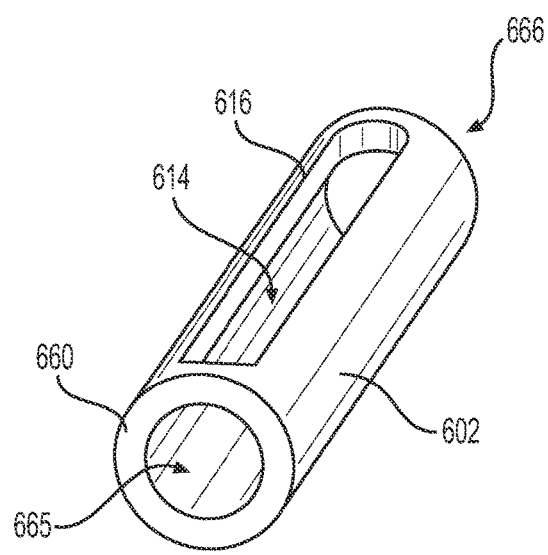
FIG. 7 illustrates a perspective view of a portion of the medical device of FIG. 6, according to aspects of this disclosure.

FIG. 4 illustrates a perspective view of another exemplary medical device 400 similar to medical devices 100, 200, and 300. Medical device 400 may include a cylindrical body 402 and ends 404, 406. Ends 404, 406 may include concave portions 408, 410. Cylindrical body 402 may be hollow and may include an opening 416 and interior portion 414. Opening 416 may be oval-shaped and may extend longitudinally within cylindrical body 402. In other examples, opening 416 may be any suitable shape and/or may be configured to receive a suture. Cylindrical body 402 may be hollow (as shown in the cylindrical body 602 of FIG. 7) and may be configured to receive extensions 417, 419 of each end 404, 406. In some examples, cylindrical body 402 may be configured to receive extensions 417, 419 at openings, like the openings 665, 666 in body 602 of FIG. 7. End surfaces 660, 661 of cylindrical body may be configured to contact and/or be flush with a surface (such as surface 665 of end 606 in FIG. 8) of one of ends 404, 406.

FIG. 5 illustrates a perspective view of an exemplary end 404 including a concave portion 410 and a cylindrical, solid extension 419. Cylindrical extension 419 may be configured to be inserted into cylindrical portion 402 and positioned within cylindrical portion 402. In some examples, cylindrical extension 419 may include an end face 423 with a recess 421. Recess 421 of end face 423 may be curved and/or contoured, and may extend from one side of extension 419 to an opposite side of 419. A longitudinal axis of recess 421 may be perpendicular to a longitudinal axis of device 200 that extends from end 404 to end 406. Recess 406 may be configured to receive a portion of a suture. Recess 421 may be present on each extension 417, 419 of each end 404, 406 and may create a space between opposing end faces of each extension 417, 419 when positioned within cylindrical body 402. That space has a smaller diameter than a diameter of a suture used with medical device 400. In other examples, cylindrical extension 419 may not include recess 421. In some examples, when medical device 400 is assembled, a suture (such as suture 120) may be positioned within an interior portion of cylindrical body 402, through opening 416, and between each extension 417, 419 of each end 404, 406. Extensions 417, 419 may pinch the suture within cylindrical body 402 to hold the suture in place. The end faces of each end 404, 406 may form an opening 412 into an interior portion of cylindrical body 402, and opening 412 may be configured to receive the suture. In some examples, a suture may be held within cylindrical body 402 and between extensions 417, 419 by the interference and/or deformation of the suture between extensions 417, 419. In some examples, portions of ends 404, 406 may be welded to cylindrical body 402 after a suture is pinched and/or fixedly positioned between extensions 417, 419. In some examples, end face 423 and/or recess 421 of one or more ends 404, 406 may be textured to increase friction between extension 417, 419 and a suture. In some examples, end face 423 and/or recess 421 may include a sharp protrusion configured to couple with a suture, such as by piercing a suture to hold the suture in place. In some examples, end face 423 may be angled relative to opening 416 such that the distance between end faces 423 of each extension 417, 419 varies when medical device 400 is assembled. For example, end face 423 may be angled relative to the radially-outer surface of extension 419 and end face 423 may be slanted such that, when medical device 400 is assembled, the distance between end faces 423 of each extension 417, 419 becomes larger as the distance from opening 416 increases, or vis-versa. In other examples, ends 404, 406 may be coupled to cylindrical body with glue, cement, or any other adhesive. In some examples, either end 404 or 406 may be integrally formed with cylindrical body and assembly of medical device 400 with a suture may only require the other end, either 406 or 404, to be inserted into cylindrical body to pinch a suture. When fully assembled, medical device 400 may fix an end of a suture within cylindrical body 402.

Figure 6:
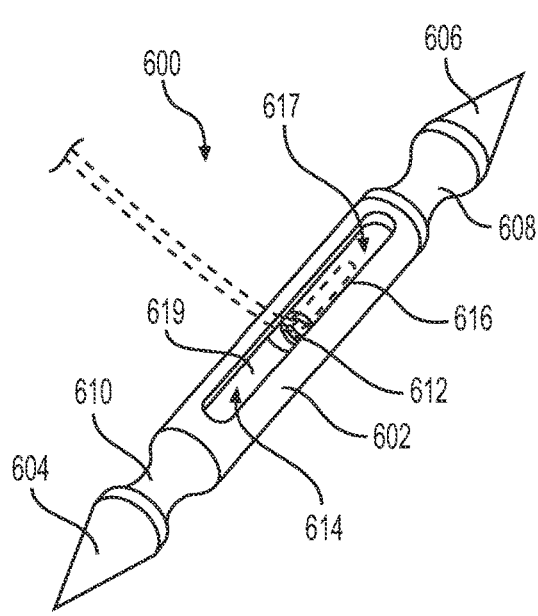
FIG. 6 illustrates a perspective view of an exemplary medical device, according to aspects of this disclosure.

FIG. 6 illustrates a perspective view of another exemplary medical device 600 similar to medical devices 100, 200, 300, and 400. Medical device 600 may include a cylindrical body 602 and ends 604, 606. Ends 604, 606 may include concave portions 608, 610 and may have extensions 617, 619 similar to those discussed above in relation to medical device 400, except for differences described herein. Cylindrical body 602 may be hollow (shown in FIG. 7) and may include an opening 616 and an interior portion 614. Opening 616 may be oval-shaped and may extend longitudinally within cylindrical body 602. In other examples, opening 616 may be any suitable shape, such as a circle, a square, a rectangle, etc. Cylindrical body 602 may be configured to receive extensions 617, 619 of each end 604, 606, and extensions 617, 619 may be positioned within openings 665, 666. In some examples, components of medical device 600 may include cylindrical body 602 and ends 604, 606.

Figure 8:
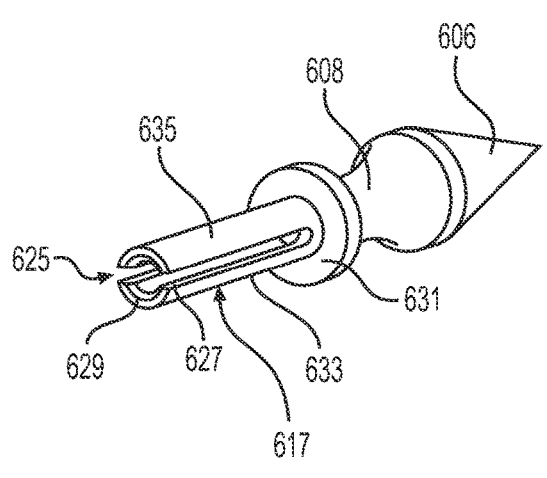
FIG. 8 illustrates a perspective view of a portion of the medical device of FIG. 6, according to aspects of this disclosure.

FIG. 8 illustrates a perspective view of end 606 of medical device 600, including extension 617. In some examples, extension 617 may be cylindrically shaped and may have a hollow body defining a lumen 626 therethrough. A first portion 633 and a second portion 635 of extension 617 may extend longitudinally from end 629 towards the opposite end 631 of extension 617, and may form two opposing gaps 625, 627 in extension 617. Extension 617 may form a collet that receives a suture in lumen 626 (such as suture 640 shown in dotted-lines in FIG. 6). Extension 617 may be configured to be inserted into cylindrical body 602 of medical device 600.

In some examples, surface 665 of end 606 may be transverse to the radially-outer surface of extension 617 and may be configured to stop insertion of end 606 into body 602. For example, when surface 665 contacts one of end surfaces 660, 661 of body 602, surface 665 may prevent end 606 from being inserted further into interior portion 614 and may facilitate proper positioning of end 606.

First portion 633 and second portion 635 of extension 617 may be curved and may form a partial cylindrical shape. In some examples, the cross-sectional diameter of extension 617, or the cross-sectional diameter of the partial cylindrical shape formed by first portion 633 and second portion 635 of extension 617, may be approximately equal to the inner diameter of cylindrical body 602, or the cross-sectional diameter of inner portion 614. In other examples, the cross-sectional diameter of extension 617 may be larger than the inner diameter of cylindrical body 602. In other examples, the cross-sectional diameter of extension 617 may decrease from end 629 to end 631, such as decreasing from a cross-sectional diameter larger than the cross-sectional diameter of inner portion 614 of body 602 at end 629 to a cross-sectional diameter approximately equal to the cross-sectional diameter of inner portion 614 at end 631.

The diameter of lumen 626 formed by first portion 633 and second portion 635 of extension 617 may be sufficiently large to permit insertion of suture 640 therein, but the diameter of lumen 626 may be made smaller as described herein the squeeze suture 640 and thereby secure suture 640 therein. In some examples, to couple a suture to medical device 600, a user may insert an end of a suture 640 into lumen 626, which may require the user to bend or move first portion 633 and second portion 635 radially outward to position the suture 640 within lumen 626. When positioned within lumen 626, first and second portions 633, 635 may exert a force on suture 640 and/or may clamp down onto suture 640. In some examples, to couple a suture 640 to medical device 600, a user may first insert a suture 640 through opening 616 and one of the ends of cylindrical body 602, and then position the suture 640 within lumen 626 of extension 617. Once positioned within lumen 626, the user may position extension 617 within the interior portion 614 of body 602, which may require the user to push first portion 633 and/or second portion 635 radially inward to fit extension 617 within the interior portion 614 of body 602. In some examples, the radially-outer cross-sectional diameter of extension 617 may increase from end 629 to end 631, which may cause a force exerted by first and second portions 633, 635 on the suture 640 to increase as the user inserts extension 617 into cylindrical body 602. This design may facilitate fixedly coupling the suture 640 to medical device 600. In other examples, the cross-sectional diameter of extension 617 may remain constant from end 629 to end 631 and may be larger than the inner diameter of body 602. When the cross-sectional diameter of extension 617 remains constant from end 629 to end 631 and is larger than the inner diameter of body 602, the user may push first and second portions 633, 635 radially inward to allow extension 617 to be inserted into body 602 and, once inserted, the inner surface of body 602 may prevent first and second portions 633, 635 from moving radially outward and may hold suture 640 positioned in lumen 626 between first and second portions 633, 635. Inserting extension 617 into body 602 may provide a pinching or clamping mechanism to pinch or clamp a suture 640 between first and second portions 633, 635 and within lumen 626.

Figure 9:
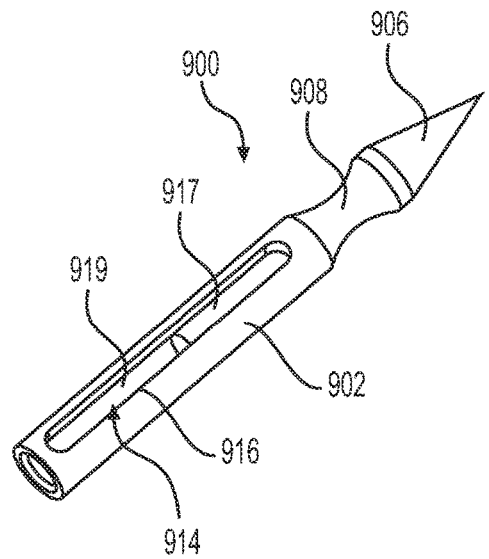
FIG. 9 illustrates a perspective view of a portion of an exemplary medical device, according to aspects of this disclosure.

In some examples, medical device 600 may also include end 604 including a solid cylindrical extension similar to end 404. Alternatively, end 604 and cylindrical body 602 may be integral with each other and may form a single component of medical device 600. As shown in FIG. 9, needle suture component 900 includes a cylindrical body 902, end 906, concave portion 908, opening 916, extension 917, and interior portion 914 similar to previously described embodiments of cylindrical bodies and ends. Needle suture component 900 may be integrally formed such that cylindrical body 902 and end 906 form a single component for use in a suture needle device. For example, medical device 600 may be assembled using end 606 (shown in FIG. 8) and needle suture component 900, allowing medical device 600 to include two components, a needle suture component 900 and an end 606, instead of three, a cylindrical body 602 and two ends 604, 606. In some examples, needle suture component 900 may be metal or any other suitable biocompatible material.

In use of any of the aforementioned embodiments of medical devices, a user may locate a treatment site (such as a wound or a cut in tissue) present in a subject's body. Any of the aforementioned medical devices may be inserted through a portion of the patient's tissue at the treatment site and then subsequently inserted into a different portion of tissue of the patient. The user may pull the two portions of the tissue penetrated by the medical device together using a suture attached to the medical device. For example, the user may thread the suture through tissue of the patient and sew tissue together to facilitate wound healing.

It should be understood that one or more of the aspects of any of the medical devices described herein may be used in combination with any of the other aspects. It also should also be understood that one or more aspects of any of the medical devices described herein may be used for suturing, stitching, cutting, grabbing, holding, moving, dissecting, or treating tissue in any part of the human body. For example any of the medical devices described herein may be used in medical procedures such as for endoluminal surgery, endoscopic submucosal dissection (ESD), cancer treatment, and/or other procedures where grabbing, moving, holding, or removing tissue is needed.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

We claim:

1. A medical device, comprising:
   a hollow cylindrical body having a longitudinal axis extending between first and second ends of the hollow cylindrical body, the hollow cylindrical body including an opening extending parallel to the longitudinal axis;
   a first end portion disposed at the first end of the hollow cylindrical body, wherein the first end portion includes a first extension extending from an inner-facing surface of the first end portion; and a second end portion disposed at the second end of the hollow cylindrical body, wherein the second end portion includes a second extension extending from an inner-facing surface of the second end portion;

wherein:

the first extension and the second extension are configured to be inserted into a lumen extending through the hollow cylindrical body;

the first extension includes a first extension portion and a second extension portion each extending longitudinally from the inner-facing surface of the first end portion, with the first extension portion spaced from the second extension portion to define: (1) a first gap between first edges of the first extension portion and the second extension portion, (2) a second gap opposite to the first gap and between second edges of the first extension portion and the second extension portion, and (3) an extension lumen between inner surfaces of the first extension portion and the second extension portion, for receipt of a suture;

the device is configured such that in an at-rest position of the first end portion without the suture in the extension lumen, a free end of the first edge of the first extension portion does not contact a free end of the first edge of the second extension portion;

the first extension portion and the second extension portion are movable into the lumen extending through the hollow cylindrical body and the medical device has a first configuration with the first end portion outside the hollow cylindrical body and having a first outer diameter larger than an inner diameter of the opening of the hollow cylindrical body, and a second configuration with the first end portion within the lumen extending through the hollow cylindrical body and having a second outer diameter fitting within the inner diameter of the opening of the hollow cylindrical body with the first extension clamping the suture to hold the suture within the first extension.

2. The medical device of claim 1, wherein the first edge of the first extension portion and the first edge of the second extension portion extend linearly.

3. The medical device of claim 2, wherein the first extension portion and the second extension portion each includes a partial cylindrical profile, thereby forming the extension lumen between the first extension portion and the second extension portion.

4. The medical device of claim 3, wherein the extension lumen between the first extension portion and the second extension portion is configured to receive the suture therein, and wherein the first extension portion and the second extension portion are each configured to exert a force on the suture to fix a position of the suture within the extension lumen between the first extension portion and the second extension portion.

5. The medical device of claim 2, wherein the first extension portion and the second extension portion are each configured to be bent radially outward with respect to a central longitudinal axis of the first extension.

6. The medical device of claim 2, wherein an inner surface of the lumen extending through the hollow cylindrical body is configured to restrict radially outward movement of the first extension portion and the second extension portion.

7. The medical device of claim 1, wherein a cross-sectional diameter of the first extension is approximately equal to an inner diameter of the hollow cylindrical body.

8. The medical device of claim 1, wherein a cross-sectional diameter of the first extension is larger than an inner diameter of the hollow cylindrical body.

9. The medical device of claim 1, wherein a cross-sectional diameter of the first extension decreases from a first end of the first extension to a second end of the first extension.

10. The medical device of claim 1, wherein the first extension is configured to form a collet with the hollow cylindrical body, and wherein the collet is configured to receive the suture.

11. A medical device, comprising:
a hollow cylindrical body having a longitudinal axis extending between first and second ends of the hollow cylindrical body, the hollow cylindrical body including an opening extending parallel to the longitudinal axis; and a first end portion disposed at the first end of the hollow cylindrical body, the first end portion comprising:
a first sharp tip configured to pierce tissue and a first inner-facing surface disposed opposite the first sharp tip; and
a first extension extending from the first inner-facing surface of the first end portion;

wherein the first extension includes a first extension portion extending longitudinally from the first inner-facing surface toward a first end of the first extension and a second extension portion extending longitudinally from the first inner-facing surface toward the first end of the first extension, wherein, the device is configured such that in an at-rest position of the first end portion without a suture within the first end portion, a free end of the first extension portion does not contact a free end of the second extension portion; and wherein the medical device has a first configuration with the first end portion outside the hollow cylindrical body and having a first outer diameter larger than an inner diameter of the opening of the hollow cylindrical body, and a second configuration with the first end portion within a lumen extending through the hollow cylindrical body and having a second outer diameter fitting within the inner diameter of the opening of the hollow cylindrical body and clamping the suture between the first extension portion and the second extension portion.

12. The medical device of claim 11, wherein the first extension portion and the second extension portion are spaced apart from each other thereby forming a first gap between the first extension portion and the second extension portion and a second gap between the first extension portion and the second extension portion, and wherein the first gap is disposed opposite the second gap.

13. The medical device of claim 11, further comprising a second end portion disposed at a second end of the hollow cylindrical body, the second end portion comprising a second sharp tip configured to pierce the tissue and a second inner-facing surface disposed opposite the second sharp tip.

14. The medical device of claim 13, wherein the second end portion further comprises a second extension extending from the second inner-facing surface of the second end portion, and wherein the second extension is configured to be inserted into the lumen extending through the hollow cylindrical body.

15. The medical device of claim 13, wherein the first sharp tip and the second sharp tip point in opposite directions.

16. The medical device of claim 11, wherein a cross-sectional diameter of the first extension is approximately equal to an inner diameter of the hollow cylindrical body.

17. The medical device of claim 11, wherein a cross-sectional diameter of the first extension is larger than an inner diameter of the hollow cylindrical body.

18. The medical device of claim 11, wherein a cross-sectional diameter of the first extension decreases from the first end of the first extension to a second end of the first extension.

19. The medical device of claim 11, wherein the first extension is configured to form a collet with the hollow cylindrical body, and wherein the collet is configured to receive the suture.

20. A medical device, comprising:
- a hollow cylindrical body having a longitudinal axis extending between first and second ends of the hollow cylindrical body, the hollow cylindrical body including an opening extending parallel to the longitudinal axis, between the first and second ends, and through a side of the hollow cylindrical body, wherein a body lumen extends within the hollow cylindrical body along the longitudinal axis; and
- a first end portion disposed at the first end of the hollow cylindrical body;

wherein:
the first end portion includes a first extension extending from an inner-facing surface of the first end portion and insertable into the body lumen extending through the hollow cylindrical body;
the first extension includes first and second extension portions extending longitudinally from the inner-facing surface of the first end portion toward a first end of the first extension with the first extension portion spaced from the second extension portion to define: (1) a first gap between first edges of the first extension portion and the second extension portion, (2) a second gap opposite to the first gap and between second edges of the first extension portion and the second extension portion, and (3) an extension lumen between inner surfaces of the first extension portion and the second extension portion, for receipt of a suture;
the device is configured such that in an at-rest position of the first end portion without the suture in the extension lumen, a free end of the first edge of the first extension portion does not contact a free end of the first edge of the second extension portion; and
the medical device has a first configuration with the first end portion outside the hollow cylindrical body and having a first outer diameter larger than an inner diameter of the opening of the hollow cylindrical body, and a second configuration with the first end portion within the body lumen of the hollow cylindrical body and having a second outer diameter fitting within the inner diameter of the opening of the hollow cylindrical body and clamping the suture between the first extension portion and the second extension portion to hold the suture with respect to the first end portion and the hollow cylindrical body.

* * * * *